US010639311B2

(12) United States Patent
Carlsson et al.

(10) Patent No.: US 10,639,311 B2
(45) Date of Patent: *May 5, 2020

(54) METHODS FOR INCREASING BLOOD PLASMA 2'-DEOXYURIDINE (DURD) AND THYMIDYLATE SYNTHASE INHIBITION

(71) Applicant: Isofol Medical AB, Göteborg (SE)

(72) Inventors: Göran U. Carlsson, Jonsered (SE); Bengt Gustavsson, Västra Froelunda (SE); Elisabeth Odin, Gothenburg (SE); Yvonne Wettergren, Göteborg (SE); Anders Vedin, Göteborg (SE)

(73) Assignee: Isofol Medical AB, Göteborg (SE)

( * ) Notice: Subject to any disclaimer, the term of this patent is extended or adjusted under 35 U.S.C. 154(b) by 0 days.

This patent is subject to a terminal disclaimer.

(21) Appl. No.: 16/266,960

(22) Filed: Feb. 4, 2019

(65) Prior Publication Data

US 2019/0240224 A1 Aug. 8, 2019

Related U.S. Application Data

(63) Continuation of application No. 15/893,235, filed on Feb. 9, 2018, now Pat. No. 10,292,984.

(60) Provisional application No. 62/458,686, filed on Feb. 14, 2017.

(51) Int. Cl.
| | | |
|---|---|---|
| *A61K 31/519* | (2006.01) | |
| *A61K 45/06* | (2006.01) | |
| *A61K 31/4745* | (2006.01) | |
| *A61K 31/513* | (2006.01) | |
| *A61K 31/555* | (2006.01) | |
| *A61P 35/00* | (2006.01) | |
| *A61K 39/395* | (2006.01) | |
| *C07K 16/22* | (2006.01) | |
| *A61K 9/00* | (2006.01) | |
| *A61K 31/282* | (2006.01) | |
| *A61K 31/4545* | (2006.01) | |
| *A61K 39/00* | (2006.01) | |

(52) U.S. Cl.
CPC .......... *A61K 31/519* (2013.01); *A61K 9/0019* (2013.01); *A61K 31/282* (2013.01); *A61K 31/4545* (2013.01); *A61K 31/4745* (2013.01); *A61K 31/513* (2013.01); *A61K 31/555* (2013.01); *A61K 39/395* (2013.01); *A61K 39/3955* (2013.01); *A61K 39/39558* (2013.01); *A61K 45/06* (2013.01); *A61P 35/00* (2018.01); *C07K 16/22* (2013.01); *A61K 2039/505* (2013.01); *A61K 2039/545* (2013.01); *C07K 2317/24* (2013.01); *C07K 2317/76* (2013.01)

(58) Field of Classification Search
CPC .................................................. A61K 31/519
See application file for complete search history.

(56) References Cited

U.S. PATENT DOCUMENTS

| | | | |
|---|---|---|---|
| 5,534,519 A | 7/1996 | Spears et al. | |
| 7,799,782 B2 | 9/2010 | Munson et al. | |
| 9,675,617 B2 | 6/2017 | Gustavsson et al. | |
| 10,292,984 B2 * | 5/2019 | Carlsson .............. | A61K 31/555 |

FOREIGN PATENT DOCUMENTS

| | | |
|---|---|---|
| EP | 3305318 A1 | 4/2018 |
| WO | WO-2005/097086 A2 | 10/2005 |
| WO | WO-2007/064968 A2 | 6/2007 |
| WO | WO-2008109349 A1 | 9/2008 |

OTHER PUBLICATIONS

C.P. Spears et al., "Rapid and complete thymidylate synthase (TS) inhibition in tumors after fluorouracil (5-FU) by methylenetetrahydrofolate (ch2fh4) preloading," 38(Supp. 7) Eur. J. Cancer S22 (2002).
K.M. Li et al., "Altered deoxyuridine and thymidine in plasma following capecitabine treatment in colorectal cancer patients," 63(1) Br. J. Clin. Pharmacol. 67-74 (2007) (published online Jul. 7, 2006. doi: 10.1111/j.1365-2125.2006.02710.x).
E. Odin et al., "Simultaneous quantification of deoxyuridine, fluorodeoxyuridine and 5-fluorouracil in plasma samples by using a LC-MS/MS method," 51(Supp. 3) Eur. J. Cancer S93 (2015) (abstract and poster).
Muhammad Wasif Saif et al., "Phase III Multicenter Randomized Clinical Trial to Evaluate the Safety and Efficacy of CoFactor/5-Fluorouracil/Bevacizumab Versus Leucovorin/5-Fluorouracil/Bevacizumab as Initial Treatment for Metastatic Colorectal Carcinoma," Clinical Colorectal Cancer, vol. 6, No. 3, 229-234 (2006).
Extended European Search Report dated Nov. 29, 2017, issued in Application No. 17187684.0.
Extended European Search Report dated Nov. 29, 2017, issued in Application No. 17187682.4.
Osamu Shinto et al., CAS: 154:351367 (2010).
Bengt Gustavsson et al., "Phase 1 dose de-escalation trial of the endogenous folate [6R]-5,10-methylene tetrahydrofolate in combination with fixed-dose pemetrexed as neoadjuvant therapy in patients with resectable rectal cancer," Investigational New Drugs, vol. 33, No. 5, pp. 1078-1085 (2015).
Yvonne Wettergren et al., "A pharmacokinetic and pharmacodynamic investigation of Modufolin® compared to Isovorin® after single dose intravenous adminislretion to patients with colon cancer: a randomized study," Cancer Chemotherapy and Pharmacology, vol. 75, No. 1, pp. 37-47 (2015).
Peter V. Danenberg et al., "Folates as adjuvants to anticancer agents: Chemical rationale and mechanism of action," Critical Reviews in Oncology /Hematology, vol. 106, pp. 118-131 (2016).

(Continued)

*Primary Examiner* — Rei Tsang Shiao
(74) *Attorney, Agent, or Firm* — Covington & Burling LLP; Einar Stole; Priscilla G. Dodson

(57) ABSTRACT

The present invention provides methods for increasing plasma dUrd levels comprising the administration of 6R-MTHF. The methods of increasing plasma dUrd increase dUrd levels compared to equimolar concentrations of LV. The present invention also provides methods for increasing TS inhibition comprising the administration of 6R-MTHF. The present invention also provides methods for increasing TS inhibition comprising the administration of 6R-MTHF.

13 Claims, 4 Drawing Sheets

(56) References Cited

OTHER PUBLICATIONS

Isofol Medical Ab, "Modufolin in Combination with 5-Fluorouracil Alone or Together with Oxaliplatin or Irinotecan in Colorectal Cancer," ClinicalTrials.gov, pp. 1-4 (Jan. 11, 2017).
Notification of Transmittal, International Search Report, and Written Opinion, dated Jul. 30, 2018 in PCT/IB2018/000206.
G. Carlsson et al., "Phase I-II study of weekly 5-fluorouracil and 5,10-methylene-tetrahydrofolate in patients with advanced gastrointestinal and breast cancer," 10(5) Cancer Journal 266-73 (1997).
Notification of Transmittal, International Search Report, and Written Opinion, dated May 13, 2019 in PCT/IB2019/000008.

* cited by examiner

METHODS FOR INCREASING BLOOD PLASMA 2'-DEOXYURIDINE (DURD) AND THYMIDYLATE SYNTHASE INHIBITION

The instant application is a continuation, and claims the benefit under 35 U.S.C. § 120, of U.S. application Ser. No. 15/893,235, filed Feb. 9, 2018, which claims priority under 35 U.S.C. § 119 to U.S. Provisional Application Ser. No. 62/458,868 filed Feb. 14, 2017, each of which is incorporated herein by reference in its entirety.

FIELD OF THE INVENTION

The present invention relates to the treatment of solid tumors in humans such as cancer, which involves the administration of [6R]-5,10-methylene tetrahydrofolate (6R-MTHF) in 5-fluorouracil (5-FU) based chemotherapy.

BACKGROUND OF THE INVENTION

5-Fluorouracil (5-FU) was first introduced in 1957 and remains a mainstay in treatment of solid tumors including colorectal cancer (CRC). 5-FU exerts cytotoxic activity primarily through inhibition of thymidylate synthase (TS) and to some extent also through incorporation of metabolites into RNA. (Ford et al. (2002) *Clinical Cancer Research* 2002; 8(1): 103-109). The overall response rate of 5-FU alone is quite limited (10-15%) and modulation strategies have been developed to increase the anticancer activity of 5-FU. (Johnston et al. *Anticancer Drugs* 2001, 12: 639-646). One of the most widely used strategies involves the co-administration of the folate 5-formyl tetrahydrofolate (folinic acid or leukovorin or LV) with 5-FU. (Romanini et al. (1991) *Cancer Res.*, 51: 789-793; Keyomarsi et al. (1988) *J. Biol. Chem.*, 263: 14402-14409). LV stabilizes the ternary complex that inhibits thymidylate synthase (TS), an enzyme necessary for DNA synthesis. (Longley et al. (2003) *Nat. Rev. Cancer*, 3(5):330-8). By adding LV to 5-FU the overall response rates increased to over 20%. (Id.).

A reduced folate, fotrexorin calcium (CoFactor®) ((dl)-5,10,-methylenepteroyl-monoglutamate calcium salt, or [6R,S]-5,10-methylene-THF Ca salt), also known as racemic methyleneTHF, has been suggested as an alternative to LV based on the assumption that direct administration of the reduced folate methyleneTHF in place of LV might offer significant advantages with respect to clinical activity. CoFactor® is a 1:1 mixture of the two diastereoisomers (Odin, E., Carlsson, G., Frösing, R., Gustaysson, B., Spears, C. P., Larsson, P. A., 1998. Chemical stability and human plasma pharmacokinetics of reduced folates. Cancer Invest. 16, 447-455). As the [6R]-isomer is the directly active co-substrate of TS, it was anticipated that the administration of CoFactor®, instead of leukovorin, would be advantageous due to lower inter- and intrapatient variability regarding both clinical safety and efficacy.

Indeed, in a Phase II Trial in previously untreated metastatic colorectal cancer, the response rate for CoFactor® was found to be 35% (Saif, M. W, Merritt, J, Robbins J, Stewart J., Schupp, J, 2006. Phase III Multicenter Randomized Clinical Trial to Evaluate the Safety and Efficacy of CoFactor®/5-Fluorouracil/Bevacizumab Versus Leucovorin/5-Fluorouracil/Bevacizumab as Initial Treatment for Metastatic Colorectal Carcinoma Clinical Colorectal Cancer, Vol. 6, No. 3, 229-234, 2006), and in another phase I/II clinical trial it was demonstrated that CoFactor® combined with 5-FU showed clinical benefit in pancreas cancer, defined as stable disease or tumor response, in 40% of patients (Saif, M. W., Makrilia N., Syrigos K., 2010. CoFactor: Folate Requirement for Optimization of 5-Fluouracil Activity in Anticancer Chemotherapy. Journal of Oncology Vol. 1-5). However, apart from presenting an unnecessary hepatic detoxification burden, the unnatural (6S)-isomer is a partial competitive inhibitor of the natural [6R]-isomer regarding its effect as co-substrate for TS (Leary, R. P., Gaumont, Y., Kisliuk, R. L., 1974. Effects of the diastereoisomers of methylenetetrahydrofolate on the reaction catalyzed by thymidylate synthetase. Biochem. Biophys. Res. Commun. 56, 484-488). Furthermore, in a Phase IIb study CoFactor® in colorectal cancer was not demonstrated to be more efficacious than leucovorin as no significant differences between the study arms with regard to either efficacy or safety could be found, and a planned Phase III study colorectal cancer was discontinued before completion (Press release: ADVENTRX Provides Update on Cofactor Program. Nov. 2, 2007).

There remains a great need for compositions and methods for stabilizing the ternary complex and enhancing the inhibition of TS. The inventors have surprisingly discovered that administration of 6R-MTHF increases plasma levels of 2'-deoxyuridine (dUrd) compared to the administration of equimolar concentrations of LV. Surprisingly, the inventors have discovered that administration of 6R-MTHF increases the inhibition of TS compared to the administration of equimolar concentrations of LV.

SUMMARY OF THE INVENTION

The inventors have discovered that equimolar doses of 6R-MTHF surprisingly produces significantly higher levels of dUrd in blood plasma compared to with LV when co-administered with 5-FU. The elevation of plasma 2'-deoxyuridine (dUrd) is a marker of TS inhibition. (Ford et al (2002) *Clinical Cancer Research*, 8(1): 103-109). The present invention surprisingly provides methods for increasing plasma dUrd levels comprising the administration of 6R-MTHF. The methods of increasing plasma dUrd increase levels compared to equimolar concentrations of LV. The present invention also provides methods for increasing TS inhibition comprising the administration of 6R-MTHF.

Plasma dUrd elevation as a surrogate marker of TS-inhibition has progressively become the biomarker of choice. The analysis is also relatively simple to perform, by blood sampling and LC-MS/MS analysis. Treatment with TS inhibitors, like 5-FU, causes a rise in intracellular pools of the TS substrate dUMP, which is reflected in raised levels of the corresponding nucleoside dUrd, which is largely extracellular and can be measured in the plasma. Furthermore, elevations of plasma dUrd have been shown to follow administration of TS inhibitors, and is thus a surrogate marker of TS inhibition (Ford et al (2002)).

The elevation of plasma dUrd levels is understood by the inventors to directly mirror the current integrated tumor TS-inhibitory state in the body during 5-FU treatment, reflecting all existing tumor sites including metastases.

The above is strongly supported by the findings that the basic activity of TS in tumors is much higher than in mucosa and that both binding of the metabolite 5-fluorodeoxyuridine monophosphate (FdUMP) to TS and TS-inhibitory effect during 5-FU treatment is very much higher in tumors than in mucosa and other cells of the body. It is notable that nearly no binding of FdUMP is observed in tumors without the addition of exogenous folate (MTHF)(Peters et al. (1991) *Eur J Cancer*, 27(3): 263-267).

Thus, the plasma dUrd level as a surrogate marker for TS inhibition clearly stands out against older assays based on e.g. $^3$H-FdUMP TS-binding, which are only confined to in vitro studies of e.g. biopsies of tumors or mucosa, or of isolated TS-enzyme. These radiolabel-based binding assays are today rarely if ever used and are strongly associated with very large degrees of variation (Peters et al. (1991) *Eur J Cancer*, 27(3): 263-267) as well as difficulties to get hold of necessary materials for the assays.

It is believed by the inventors that a degree of TS inhibition above 90% is necessary for the tumors to enter into the apoptosis state which is required for tumor necrosis to take place. It is further believed that 6R-MTHF has the ability to stabilize the above inhibitory ternary complex up to the level required for obtaining a TS inhibition of the 90% level and above.

DETAILED DESCRIPTION OF THE INVENTION

Figure 1:
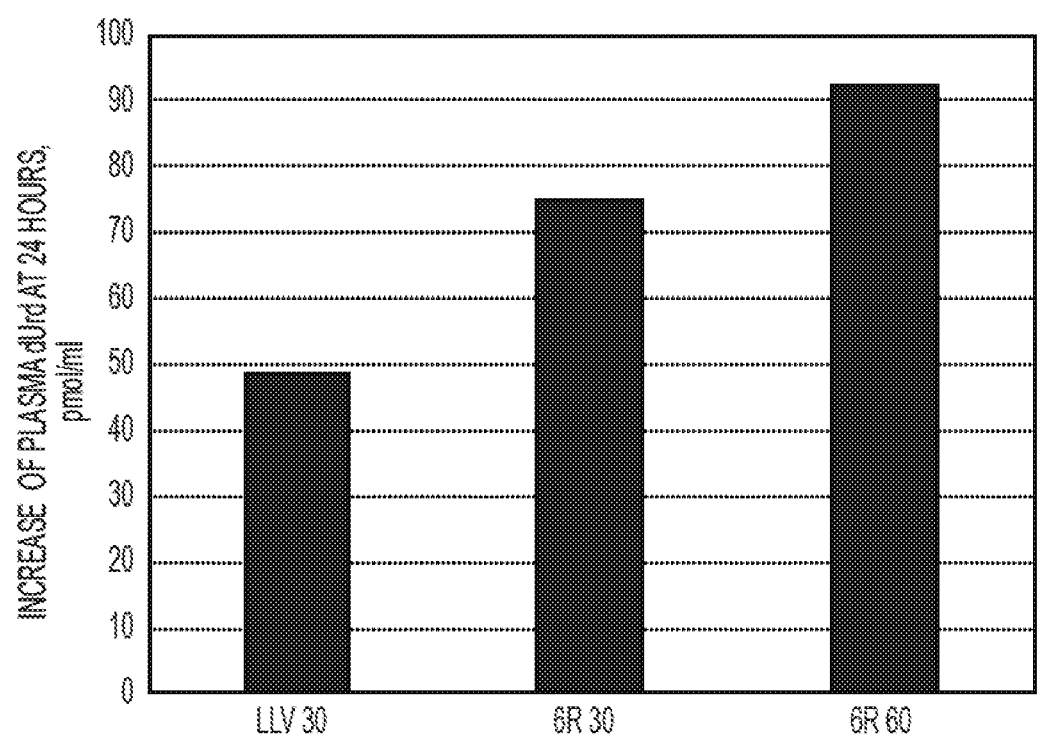
FIG. 1: Increased TS inhibition following administration of 5-FU with 30 and 60 mg/m$^2$ 6R-MTHF (denoted as "6R") compared to 30 mg/m$^2$ l-LV ("LLV") (denoted as "LLV 30") compare to 60 mg/m$^2$ racemic (d,l-LV or LV).

In one embodiment, [6R]-5,10-methylenetetrahydrofolic acid (6R-MTHF) or a pharmaceutically acceptable salt thereof is employed as a solid form which is soluble in water or as a lyophilisate, optionally stabilized by one or more suitable excipients and/or antioxidants such as citric acid or ascorbic acid or salt forms thereof. In one embodiment 6R-MTHF is administered as one or more IV boluses, each bolus containing 5-1000 mg/m$^2$ BSA (body surface area), such as 5 mg/m$^2$ BSA, such as 7 mg/m$^2$ BSA, such as 10 mg/m$^2$ BSA, such as 15 mg/m$^2$ BSA, such as 30 mg/m$^2$ BSA, such as 60 mg/m$^2$ BSA, such as 120 mg/m$^2$ BSA, such as 240 mg/m$^2$ BSA, such as 480 mg/m$^2$ BSA, such as 720 mg/m$^2$ BSA or such as 960 mg/m$^2$ BSA. As used herein, "bolus" means a method of intravenous administration wherein a single dose of a pharmaceutical composition is given all at once, unlike intravenous infusion wherein a single dose is given over at constant concentration over a period of time.

The dosage depends on the form of therapy, on the form of application of the preparation, and on the age, weight, nutrition and condition of the patient. Treatment can commence with a smaller amount, below the optimum amount, which can be increased in order to achieve the optimum effect. The preferred dose used in therapy ranges between 10 mg and 3,000 mg per day, particularly between 50 mg and 500 mg per day. Administration can be effected either as a single dose or as a repeated dose.

In one embodiment, 6R-MTHF may be in the form of a free acid, in the form of pharmaceutically acceptable salts, particularly acidic salts, as well as alkali or alkaline earth metal salts.

In another embodiment, MTHF comprises both diastereomeric isomers, particularly diastereoisomerically pure, natural 6R-MTHF. As used herein, the term "diastereoisomerically pure" means 6R-MTHF or its salt in isomeric excess over the other isomer greater than about 80%, preferably greater than about 90%, preferably greater than about 95%, more preferably greater than about 97%, even more preferably greater than about 99%, more preferably greater than about 99.5% or more, and most preferably up to 100%, wherein the remainder is the other isomer 6S-MTHF.

In another embodiment, the 6R-MTHF is chemically pure. As used herein, the term "chemically pure" means a compound in about 80% chemical purity, preferably about 90%, more preferably about 95%, more preferably about 97%, more preferably about 98% chemical purity, and most preferably 99% or higher than 99%, e.g., 99.5, 99.6, 99.7, 99.8, 99.9 or up to 100% chemical purity, as determined by HPLC. Chemical impurities may include unreacted starting material (including solvents), degradation products of 6R-MTHF (such as tetrahydrofolic acid and its degradation products), etc.

Optionally, a pharmaceutical composition comprising 6R-MTHF, for example, may further comprise at least one anticancer compound. An anticancer compound may include but is not limited to one or more chemotherapeutic agents, such as but not limited to: nucleic acids, in particular fluorinated nucleic acids (e.g. 5-flurouracil (5-FU) or an analog or prodrug thereof), antifolates (e.g. pemetrexed, raltitrexed, lometrexol), topoisomerase inhibitors (e.g. irinotecan, topotecan), antimetabolite drugs (e.g. methotrexate, gemcitabine, tezacitabine), 5-FU modulators, alkylating agents (e.g. cyclophosphamide, carmustine), nucleic acid biosynthesis inhibitors (such as mitomycin, anthracyclines (e.g. epirubicin, doxorubicin), platinum derivatives (e.g. cisplatin, oxaliplatin, carboplatin), microtubule disrupting drugs (e.g. paclitaxel, docetaxel, vinolrebine, vincristine), hormone blocking drugs (e.g. tamoxifen), inhibitors of kinases, including but not limited to receptor and nonreceptor tyrosine kinases (e.g. Iressa, Tarceva, SU5416, PTK787, Gleevec), proteosome inhibitors (e.g. bortezomib), immune modulators (e.g. levamisole), anti-inflammatory drugs, vascularization inhibitors, cytokines (e.g. interleukins, tumor necrosis factors), and drugs that inhibit the activity of cytokines, hormones, or receptors for cytokines or hormones (e.g. the anti-VEGF antibody bevacizumab or "Avastin"). Anticancer compounds may also include monoclonal antibodies, such as but not limited to monoclonal antibodies that bind cytokines, hormones, or hormone receptors (e.g. antibodies that block activation of EGF or VEGF growth factors, such as Avastin, Erbitux, herceptin), etc. In one embodiment, the 6R-MTHF is administered in combination with a therapeutically effective amount of at least one anticancer compound. When 6R-MTHF is administered in combination with a therapeutically effective amount of at least one anticancer compound a person of ordinary skill in the art would understand that the at least one anticancer compound can be administered before, after or concurrently with 6R-MTHF.

6R-MTHF doses of 30-240 mg/m² BSA are being evaluated in the presence of various permutations of the cytotoxics, 5-FU alone or 5-FU plus oxaliplatin, bevacizumab or irinotecan given at standard dose levels. The study is expected to be completed by year end 2017. A summary of the study design and each study arm is depicted below in Table 1.

TABLE 1

Initial Doses of the Chemotherapy Agents (Bevacizumab, Oxaliplatin, Irinotecan, and/or 5-FU) and of the Study Drug (6R-MTHF)

| Treatment Arm | Cohort* | Bevacizumab At approx. −180 minutes (infusion 30 to 90 min) | Oxaliplatin¶ At approx. −60 minutes (infusion 15 to 120 min) | Irinotecad# At approx. −60 minutes (infusion 30 to 90 min) | 5-FU§* At 0 minute (bolus) | 6R-MTHF At approx. 30 minutes (bolus) $^a$ | 5-FU At approx. 35 minutes (46-hour continuous infusion) $^a$ |
|---|---|---|---|---|---|---|---|
| Arm 1 | Cohort 1 | N/A | N/A | N/A | 500 mg/m² | 30 mg/m² | N/A |
|  | Cohort 2 | N/A | N/A | N/A | 500 mg/m² | 60 mg/m² | N/A |
|  | Cohort 8 | N/A | N/A | N/A | 500 mg/m² | 120 mg/m² | N/A |
|  | Cohort 9 | N/A | N/A | N/A | 500 mg/m² | 240 mg/m² | N/A |
| Arm 2 | Cohort 4 | N/A | 85 mg/m² | N/A | 500 mg/m² | 30 mg/m² | N/A |
|  | Cohort 5 | N/A | 85 mg/m² | N/A | 500 mg/m² | 60 mg/m² | N/A |
| Arm 3 | Cohort 6 | N/A | N/A | 180 mg/m² | 500 mg/m² | 30 mg/m² | N/A |
|  | Cohort 7 | N/A | N/A | 180 mg/m² | 500 mg/m² | 60 mg/m² | N/A |
| Arm 4 | Cohort 12 | N/A | 85 mg/m² | N/A | 400 mg/m² | 60 mg/m² $^a$ | 2 400 mg/m² |
|  | Cohort 13 | N/A | 85 mg/m² | N/A | 400 mg/m² | 120 mg/m² $^a$ | 2 400 mg/m² |
|  | Cohort 14 | N/A | 85 mg/m² | N/A | 400 mg/m² | 240 mg/m² $^a$ | 2 400 mg/m² |
| Arm 5 | Cohort 15 | 5 mg/kg | 85 mg/m² | N/A | 400 mg/m² | SP2D $^{a, b}$ | 2 400 mg/m² |

Abbreviation:
N/A: not applicable,
SP2D: selected phase 2 dose.
¶The time-point window for Oxaliplatin administration will be expanded to allow infusion times of up to 120 minutes, if necessary
The time-point window for Irinotecan administration will be expanded to allow infusion times of up to 90 minutes, if necessary.
§The administered bolus 5-FU dose should not surpass the maximum recommended daily dose of 1000 mg, regardless of the body surface area.
*Cohort #3, Cohort #10 and Cohort #11, originally included in earlier versions of this clinical study protocol, have been erased.
$^a$ In Treatment Arm #4 (Cohorts #12, #13, and #14) and Arm #5 (Cohort #15) the total dose of 6R-MTHF will be divided into two (2) i.v. bolus injections dispensed approximately 30 and 60 minutes after administration of 5-FU bolus injection (at 0 minute), respectively. The continuous 5-FU infusion will be paused for administration of the second injection of 6R-MTHF.
$^b$ The dose level of 6R-MTHF in Treatment Arm #4 (MOFOX) assessed as the dose level with the most favourable profile for the following investigation.

EXAMPLES

The following examples are merely indicative of the nature of the present invention, and should not be construed as limiting the scope of the invention, nor of the appended claims, in any manner.

Example 1—Treatment with 5-FU and Folates

1. Study Design.

The safety and efficacy of [6R]-5,10-methylenetetrahydrofolate ([6R]-MTHF) is analyzed in an open-label, multiple-site, Phase I/II Dose Cohort Trial (ISO-CC-005) in patients with stage IV colorectal cancer (mCRC) to determine the safe and tolerable i.v. bolus dose of 6R-MTHF in combination with standard doses of 5-FU (500 mg/m²) alone or in combination with a fixed dose of Bevacizumab, Oxaliplatin or Irinotecan in patients with stage IV colorectal cancer. Among groups of patients (n≥3) ascending In Gothenburg, for almost two decades, clinical, treatment and outcomes data on all patients with CRC have been collected. Plasma and tissue samples have been stored in a biobank under appropriate physical conditions for long term storage. The database and the biobank operate under the auspices of the relevant ethical and regulatory permissions. Patients having been treated with the standard 5-FU dose, 500 mg/m² plus i.v. bolus LV, 60 mg/m² (equivalent to 30 mg/m² of LLV) were randomly drawn from the databank.

For all patients, stored plasma samples were used for determination of dUrd.

The present study is a historical group comparison study. All patients have been treated with a standard dose of 500 mg 5-FU given as a bolus injection plus the respective folate 6R-MTHF or LV also given as bolus injections.

2. Patients Treated with 6R-MTHF.

All patients have been measured during two consecutive treatment cycles with 5-FU. Values for dUrd were measured immediately before injection of 5-FU ($t_0$) and after 24 hours ($t_{24}$). Mean values and standard deviations for differences between $t_{24}$ and to were calculated for the patients on each dose level of 30 and 60 mg/m² 6R-MTHF, respectively. Some values have also been assayed and calculated for 240 mg/m² 6R-MTHF.

3. Patients Treated with LV.

Twenty-four patients with metastatic colorectal cancer (mCRC) treated with 5-FU plus 60 mg/m² LV were drawn at random from the data base and levels of dUrd were determined at to and $t_{24}$ from two treatment cycles for each patient and the mean values and standard deviations for the differences between $t_{24}$ and to were calculated in the same way as for the 6R-MTHF patients. Since LV is a 50:50 mixture of the natural (1-formyl-tetrahydrofolate) and unnatural (d-formyl-tetrahydrofolate) isomers the active isomer constitutes one half of the LV doses given. The molecular weights for LV and 6R-MTHF are very similar and therefore 60 mg of LV may be considered as equimolar with 30 mg of 6R-MTHF.

4. Statistical Methods.

The differences between all four groups were tested by means of the Friedman two-way analysis of variance and thereafter the difference between the two equimolar groups LV 60 mg/m² and 6R-MTHF 30 mg/m² was tested by means of the Mann-Whitney U test. P-values less than 0.05 were considered significant.

3. Determination of Plasma dUrd.

Plasma dUrd was determined by a method comprising liquid chromatography followed by tandem mass spectrometry broadly summarized as follows. Plasma samples were removed from −80° C. freezer, trichloroacetic acid was added to the plasma, and the samples mixed and centrifuged. The supernatant was filtered in a 10 kDa molecular weight cut-off membrane filter and again centrifuged for 30 min. The solution at the bottom of the tube was then ready for LC-MS/MS analysis. Calibration samples were prepared in the same way using blank plasma samples and different internal standard concentrations. The injection volume into LC-MS/MS was 40 μl. Deoxyuridine and chlorodeoxyuridine were ionized by electrospray negative mode. MS parameters were optimized for maximum response of all folates. A MS/MS acquisition method (multiple reaction monitoring) was utilized.

Example 2—TS Inhibition

The differences between the first three groups were significant (p=0.04) and also the difference between the two equimolar groups LV 60 mg/m² and [6R]-MTHF 30 mg/m² (p=0.03). An equimolar dose of [6R]-MTHF together with 5-FU gives a significantly higher level of dUrd than does LV. Also, there seems to be a dose-response relationship between increasing [6R]-MTHF doses and increasing levels of TS inhibition as reflected by the increasing levels of plasma dUrd (See Table 2 and FIG. 1).

TABLE 2

Incremental dUrd at 24 hours after bolus injection of 5-FU plus LLV or 6R-MTHF

| Active compound dose mg/m2 BSA | Dose administered mg/m2 BSA | No. of cycles | Mean ($t_{24} - t_0$) plasma dUrd pmol/ml | SD pmol/ml | p < LV vs. 6R | p < All Groups[1] |
|---|---|---|---|---|---|---|
| LLV 30 | 60 (d, l-LV) | 48 | 48.7 | 25.8 | 0.03 | 0.04 |
| 6R-MTHF 30 | 30 | 18 | 74.7 | 52.7 | | |
| 6R-MTHF 60 | 60 | 16 | 91.8 | 67.6 | | |
| 6R-MTHF 240 | 240 | 4 | 99.9 | ND | | |

[1]Except for the 240 mg/m² group.

This study demonstrates that biomodulation of 5-FU with 6R-MTHF rather than LV results in higher plasma dUrd and increased TS inhibition. This observation is further supported by the dose dependent inhibition of TS after increasing doses of 6R-MTHF.

Figure 2:
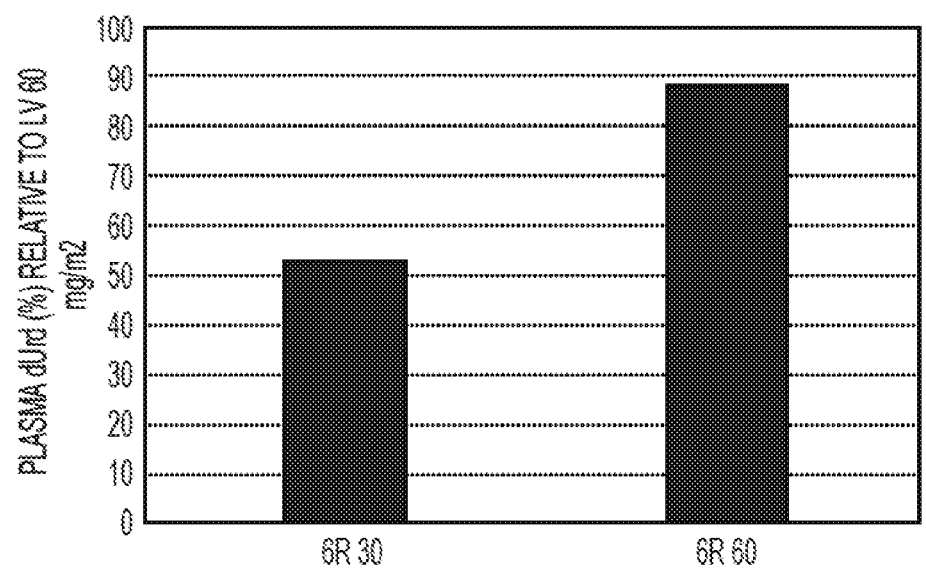
FIG. 2: Plasma dUrd levels relative to 30 mg/m$^2$ LLV (60 mg/m$^2$ of d,l-LV or LV or LV 60) following administration of 5-FU with 30 and 60 mg/m$^2$ 6R-MTHF (denoted as "6R").
Figure 3:
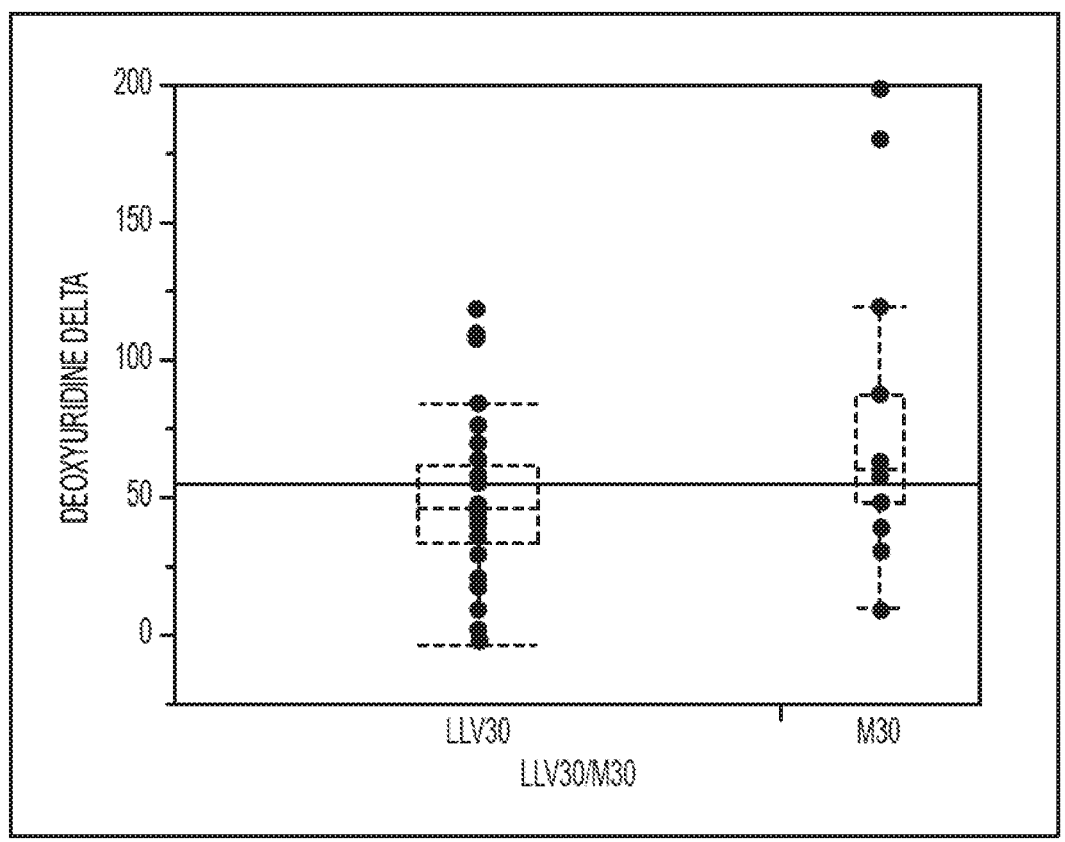
FIG. 3: Equimolar comparison of LV and 6R-MTHF shown as incremental plasma dUrd levels at 24 hours after bolus injection of 5-FU 500 mg/m$^2$ administered together with bolus injection of 30 mg/m$^2$ of l-LV (denoted as "LLV30") (60 mg/m$^2$ of d,l-LV or LV) or 30 mg/m$^2$ of 6R-MTHF (denoted as "M30"). The increments have been calculated as the individual differences between dUrd plasma concentrations at 24 hours ($t_{24}$) minus plasma dUrd concentrations immediately before injection ($t_0$) for LLV cycles (n=48) and 6R-MTHF cycles (n=18). LLV is the active natural isomer of LV which is a 50:50 mixture of LLV and the unnatural, not (significantly) active d-LV. The molecular weights of 6R-MTHF and LLV are sufficiently similar as basis for an equimolar comparison. The difference between the group has been tested with the Mann-Whitney U test (p<0.05).
Figure 4:
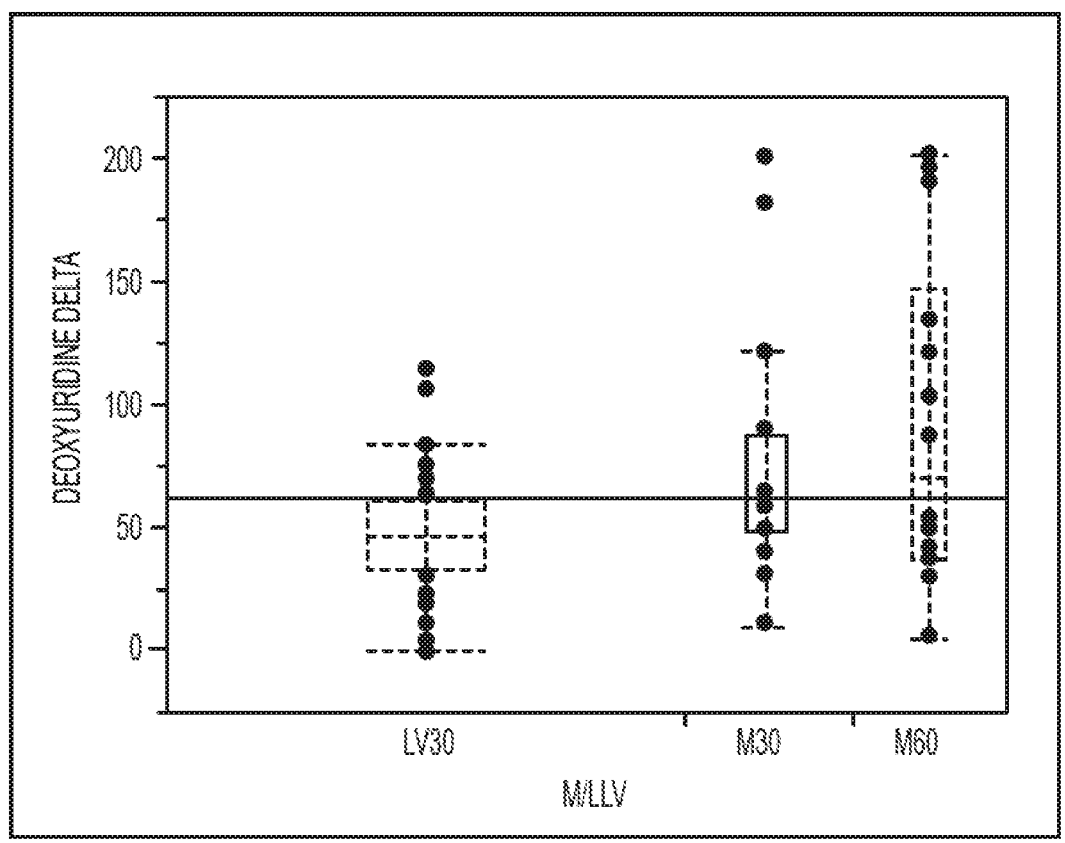
FIG. 4: 6R-MTHF dose dependent increase of incremental plasma dUrd levels at 24 hours after bolus injection of 5-FU 500 mg/m$^2$ administered together with bolus injection of 30 mg/m$^2$ LLV (denoted as "LLV30") (60 mg/m$^2$ of d,l-LV or LV) or 30 mg/m$^2$ (denoted as "M30") or 60 mg/m$^2$ of 6R-MTHF (denoted as "M60"). The increments have been calculated as the individual differences between dUrd plasma concentrations at 24 hours ($t_{24}$) minus plasma dUrd concentrations immediately before injection ($t_0$) for LLV cycles (30 mg/m$^2$ n=48) and 6R-MTHF cycles (30 mg/m$^2$ n=18; 60 mg/m$^2$ n=16). The differences between the groups were significant and have been tested with the the Friedman two-way analysis of variance (p<0.05).

The LV bolus dose of 60 mg/m² is the standard dose used in the so called Nordic treatment regime used widely in Scandinavia. Clinical results are similar to those obtained with other regimes when LV is administered by infusion, often 400 mg over two hours. (Gustaysson et al., (2015) *Clinical Colorectal Cancer*, 14: 1-10). It is interesting to note the much higher TS inhibition after 6R-MTHF (FIG. 2).

What is claimed is:

1. A method comprising:
   a. a step of administering 400 mg/m² 5-fluorouracil (5-FU) intravenously as a bolus injection to a human subject;
   b. a step of administering 60, 120, 240 mg/m² [6R]-5,10-methylene tetrahydrofolate (6R-MTHF) intravenously as two bolus injections to said human subject approximately 30 minutes and 60 minutes following step (a); and
   c. a step of administering 2400 mg/m² 5-FU as a continuous infusion, either simultaneously with or following step (b).

2. The method of claim 1, wherein said method produces an increased plasma concentration of 2'-deoxyuridine (dUrd) relative to dUrd plasma concentration in a human subject following administration of an equimolar dose of 5-formyl tetrahydrofolate (LV).

3. The method of claim 2, wherein said human subject suffers from cancer.

4. The method of claim 3, wherein said cancer is colorectal cancer.

5. The method of claim 2, further comprising the administration of a therapeutically effective amount of at least one anticancer agent selected from the group consisting of oxaliplatin, irinotecan, and bevacizumab.

6. The method of claim 1, wherein said method produces an increased inhibition of thymidylate synthase (TS) relative to TS inhibition in a human subject following administration of an equimolar dose of LV.

7. The method of claim 6, wherein said human subject suffers from cancer.

8. The method of claim 7, wherein said cancer is colorectal cancer.

9. The method of claim 6, further comprising the administration of a therapeutically effective amount of at least one anticancer agent selected from the group consisting of oxaliplatin, irinotecan, and bevacizumab.

10. The method of claim 2, wherein the 6R-MTHF has a chemical purity greater than 90% and in 95% isomeric excess over [6S]-5,10-methylene tetrahydrofolate (6S-MTHF).

11. The method of claim 6, wherein the 6R-MTHF has a chemical purity greater than 90% and in 95% isomeric excess over 6S-MTHF.

12. The method of claim 1, wherein the 6R-MTHF is provided as a pharmaceutically acceptable salt.

13. The method of claim 12, wherein the pharmaceutically acceptable salt is provided as a lyophilisate.

* * * * *